US008624064B2

(12) United States Patent
Saiki et al.

(10) Patent No.: US 8,624,064 B2
(45) Date of Patent: Jan. 7, 2014

(54) 4-HYDROXYPHENYLALKYLAMINE DERIVATIVE

(75) Inventors: Takeaki Saiki, Hiratsuka (JP); Keiji Wakita, Ichihara (JP); Yasushi Sugiura, Ichihara (JP); Yoshinori Taniguchi, Ichihara (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 217 days.

(21) Appl. No.: 12/808,855

(22) PCT Filed: Dec. 16, 2008

(86) PCT No.: PCT/JP2008/072813
§ 371 (c)(1),
(2), (4) Date: Jun. 17, 2010

(87) PCT Pub. No.: WO2009/078394
PCT Pub. Date: Jun. 25, 2009

(65) Prior Publication Data
US 2010/0280188 A1    Nov. 4, 2010

(30) Foreign Application Priority Data
Dec. 19, 2007    (JP) ................. 2007-327635

(51) Int. Cl.
C07C 211/09    (2006.01)
C07C 211/17    (2006.01)
C07C 211/18    (2006.01)
C07C 211/22    (2006.01)
C07C 211/50    (2006.01)
C07C 211/53    (2006.01)

(52) U.S. Cl.
USPC ........... 564/306; 564/367; 564/368; 564/369; 564/370; 564/371

(58) Field of Classification Search
USPC ......................................... 564/306, 367–371
See application file for complete search history.

(56) References Cited

U.S. PATENT DOCUMENTS

| | | | |
|---|---|---|---|
| 2,962,531 A | 11/1960 | Coffield | |
| 3,043,774 A | 7/1962 | Coffield | |
| 3,098,841 A * | 7/1963 | Morris Rupert C et al. .. | 524/222 |
| 3,139,341 A | 6/1964 | Schlesinger et al. | |
| 3,218,322 A | 11/1965 | Orloff | |
| 3,225,099 A | 12/1965 | Coffield | |
| 3,368,972 A * | 2/1968 | Otto Ferdinand P ......... | 508/558 |
| 3,944,397 A * | 3/1976 | Gardiner et al. ................ | 44/425 |
| 4,491,654 A * | 1/1985 | Cummings .................... | 525/490 |
| 5,039,310 A * | 8/1991 | Blain et al. ...................... | 44/424 |
| 6,919,482 B2 * | 7/2005 | Moran et al. .................. | 564/306 |
| 7,572,877 B2 * | 8/2009 | Koyama et al. ............... | 528/120 |
| 2003/0065177 A1 | 4/2003 | Sheridan et al. | |
| 2003/0125328 A1* | 7/2003 | Sikorski et al. ............... | 514/241 |

FOREIGN PATENT DOCUMENTS

| | | |
|---|---|---|
| CN | 1564823 A | 1/2005 |
| EP | 0104572 A1 | 4/1984 |
| JP | 46-43303 B1 | 12/1971 |
| JP | 47-9258 B1 | 3/1972 |
| JP | 62030134 A | 9/1987 |
| JP | 63-188689 A | 8/1988 |
| JP | 03161479 A | 11/1991 |
| JP | 05-186478 A | 7/1993 |
| JP | 09-296007 A | 11/1997 |
| JP | 2001-122883 A | 5/2001 |
| SU | 596585 A1 | 3/1978 |
| SU | 763313 A1 | 9/1980 |
| SU | 1118638 A1 | 10/1984 |

OTHER PUBLICATIONS

Derwent Abstract for SU 1118638 A.*
Derwent Abstract for SU 596585 A.*

(Continued)

*Primary Examiner* — Mike M Dollinger
(74) *Attorney, Agent, or Firm* — Howard & Howard Attorneys PLLC

(57) ABSTRACT

The present invention relates to a compound represented by the following general formula (I):

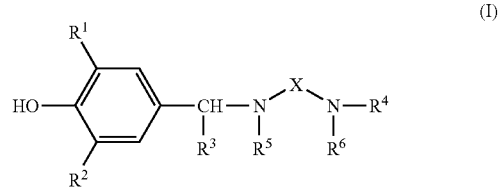

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent organic group or a group represented by the following general formula (II):

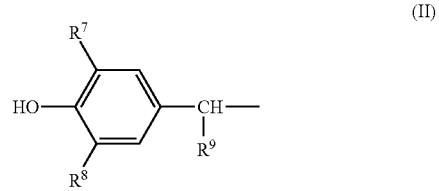

in which
$R^7$ and $R^8$ independently represent a monovalent hydrocarbon group; and
$R^9$ represents a hydrogen atom or an alkyl group having 1 to 4 carbon atoms,
with the proviso that $R^5$ and $R^6$ may combine together to form a divalent hydrocarbon group. The aforementioned compounds are useful as a polymerization inhibitor and the like.

12 Claims, No Drawings

(56) References Cited

OTHER PUBLICATIONS

Derwent Abstract for SU 763313 B.*
Zhao et al. Study on the electrochemical behavior of dopamine with poly(sulfosalicylic acid) modified glassy carbon electrode. Analytica Chimica Acta 441 (2001) 117-122.*
Vodkin et al., "Synthesis and Ultraviolet Spectra of Substituted Aminomethylenequinones," Bulletin of the Academy of Sciences of the USSR, Division of Chemical Sciences, Springer New York LLC, US No. 7, 1 Jan. 1, 1967, pp. 1592-1596.
Supplementary European Search Report for Application No. EP 08861159 dated Sep. 8, 2011, 2 pages.
Japanese Patent No. 46-43303, no english abstract available, 3 pages.
Japanese Patent No. 47-9258, no english abstract available, 8 pages.
English language abstract for JP 63-188689 extracted from espacenet.com database, dated Jul. 2, 2010, 8 pages.
English language translation and abstract for JP 05-186478 extracted from PAJ database, dated Jul. 2, 2010, 90 pages.
English language translation and abstract for JP 09-296007 extracted from PAJ database, dated Jul. 2, 2010, 32 pages.
English language translation and abstract for JP 2001-122883 extracted from PAJ database, dated Jul. 2, 2010, 29 pages.
Soviet Union Patent No. SU 596585, no english abstract available, 4 pages.
Soviet Union Patent No. SU 763313, no english abstract available, 4 pages.
Soviet Union Patent No. SU 1118638, no english abstract available, 5 pages.
PCT International Search Report for PCT/JP2008/072813, dated Jan. 27, 2009, 3 pages.
Chi, Ki-Whan et al., Synthesis of Mannich bases using substituted aromatic alcohols with secondary amines: relative reactivity and regioselectivity depending on substrates, Journal of the Korean Chemical Society, Korean Chemical Society, 2001, vol. 45, No. 1, p. 51-60, 10 pages.

* cited by examiner

4-HYDROXYPHENYLALKYLAMINE DERIVATIVE

RELATED APPLICATIONS

This application claims priority to and all the advantages of International Patent Application No. PCT/JP2008/072813, filed on Dec. 16, 2008, which claims priority to Japanese Patent Application No. JP 2007-327635, filed on Dec. 19, 2007.

TECHNICAL FIELD

The present application claims priority on the basis of Japanese Patent Application No. 2007-327635, filed in Japan on Dec. 19, 2007, which is hereby incorporated by reference.

The present invention relates to novel compounds which are useful as a polymerization inhibitor or the like.

BACKGROUND ART

Heretofore, hindered phenol-based compounds are useful as a polymerization inhibitor, an antioxidant, a thermal stabilizer, or the like, and various derivatives thereof are proposed. In particular, for use as a polymerization inhibitor, a hindered phenol-based polymerization inhibitor is widely used as an inhibitor for controlling non-preferred polymerization reactions at the time of storing monomers for a long time or synthesizing and/or purifying monomers. As examples of the aforementioned hindered phenol-based polymerization inhibitors, mention may be made of, for example, 2,6-di-t-butyl-p-cresol, 2,6-di-t-butyl-4-dimethylaminomethylphenol, and the like, as described in Patent Documents 1 to 6 shown below.

LIST OF PATENT DOCUMENTS

Patent Document 1: Japanese Unexamined Patent Application, First Publication No. H05-186478
Patent Document 2: Japanese Unexamined Patent Application, First Publication No. H09-296007
Patent Document 3: U.S. Pat. No. 3,043,774
Patent Document 4: U.S. Pat. No. 3,225,099
Patent Document 5: U.S. Pat. No. 2,962,531
Patent Document 6: US Patent Application Publication No. 2003/65177

DISCLOSURE OF INVENTION

Technical Problems

Recently, many novel polymerizable monomers have been developed. Depending on synthesis conditions, polymerization inhibitors which are stronger than conventional ones have been desired. In addition, novel fats and oils, as well as resins have also been developed. Various antioxidants and thermal stabilizers therefor are also desired.

The present invention was made under the aforementioned circumstances of the prior art, and an objective of the present invention is to provide novel compounds which can be utilized as a polymerization inhibitor, an antioxidant, a thermal stabilizer, or the like, exhibiting effects which are equivalent to or greater than the effects obtained in the prior art.

Technical Solution

An objective of the present invention can be achieved by a 4-hydroxyphenylalkylamine derivative represented by the following general formula (I):

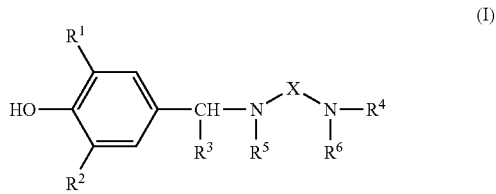

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent organic group or a group represented by the following general formula (II):

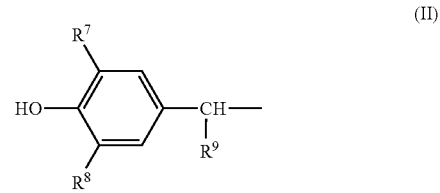

in which
$R^7$ and $R^8$ independently represent a monovalent hydrocarbon group; and
$R^9$ represents a hydrogen atom or an alkyl group having 1 to 4 carbon atoms,
with the proviso that $R^5$ and $R^6$ may combine together to form a divalent hydrocarbon group.

The aforementioned 4-hydroxyphenylalkylamine derivatives may be a compound represented by the following general formula (III):

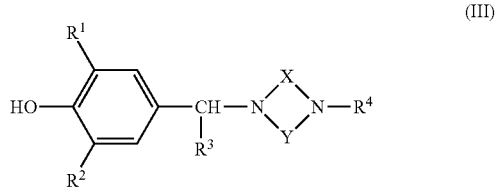

wherein
$R^1$, $R^2$, $R^3$ and $R^4$, as well as X are the same as described above; and
Y represents a divalent hydrocarbon group.

The aforementioned compounds can be used as a polymerization inhibitor, and in particular, can be used as a polymerization inhibitor of an acryloxysilane or methacryloxysilane.

In addition, the present invention relates to a polymerization inhibitor, containing the aforementioned compound; a silane coupling agent containing the aforementioned polymerization inhibitor and an acryloxysilane or a methacryloxysilane; a polymerizable composition containing the aforementioned polymerization initiator; a polymerizable composition or a polymer containing the aforementioned silane coupling agent; and a molded product obtained from the aforementioned polymerizable composition and polymer.

In addition, in the present invention, a silicon-containing compound which contains an acryloxy group or a methacryloxy group, such as acryloxysilane or methacryloxysilane can be produced in the presence of the aforementioned compound. More particularly, an acryloxysilane or methacryloxysilane can be produced by addition-reacting an acrylate or a methacrylate of an alcohol containing an aliphatic unsaturated bond with an organosilane containing a hydrogen atom binding to a silicon atom, in the presence of the aforementioned compound. The aforementioned organosilane containing a hydrogen atom binding to a silicon atom may be a methyldialkoxysilane.

In addition, in the method for producing an acryloxysilane or methacryloxysilane of the present invention, a step of purifying the acryloxysilane or methacryloxysilane by distillation in the presence of the aforementioned compound can be included.

Effects of the Invention

The compound of the present invention can be utilized as a polymerization inhibitor exhibiting effects which are the same as or greater than the effects obtained by conventional ones, and can be blended in various polymerizable compositions. The compound of the present invention can be suitably used as a polymerization inhibitor for a silicon-containing compound containing an acryloxy group or a methacryloxy group, and in particular, an acryloxysilane or methacryloxysilane.

Therefore, the compound of the present invention can be blended as a polymerization inhibitor to a silane coupling agent containing an acryloxysilane or methacryloxysilane. Thereby, polymerization of the aforementioned silane coupling agent during storage can be inhibited, and for this reason, increase of viscosity caused by the aforementioned polymerization can be prevented, and superior handling properties can be maintained for a long time. In addition, a polymerizable composition or polymer containing the aforementioned silane coupling agent exhibits superior adhesiveness, superior oxidation resistance, superior thermal stability, and the like. Therefore, a molded product exhibiting various superior physical properties such as strength, weather resistance, thermal resistance, and the like can be produced.

In addition, in a method for producing a silicon-containing compound containing an acryloxy group or methacryloxy group, such as an acryloxysilane or methacryloxysilane, of the present invention, non-preferred polymerization reactions during production or distillation thereof can be controlled. Therefore, a silicon-containing compound containing an acryloxy group or methacryloxy group, such as an acryloxysilane or methacryloxysilane, with high purity can be obtained in high yield.

BEST MODES FOR CARRYING OUT THE INVENTION

The compound of the present invention is represented by the following general formula (I):

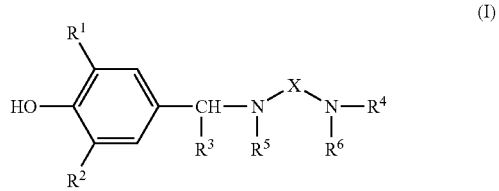

(I)

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent organic group or a group represented by the following general formula (II):

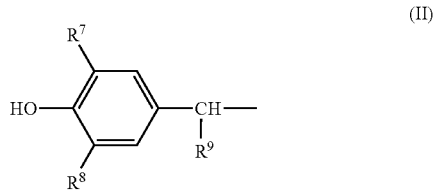

(II)

in which
$R^7$ and $R^8$ independently represent a monovalent hydrocarbon group; and
$R^9$ represents a hydrogen atom or an alkyl group having 1 to 4 carbon atoms,
with the proviso that $R^5$ and $R^6$ may combine together to form a divalent hydrocarbon group.

In addition, the compound of the present invention can also have a structure represented by the following general formula (III):

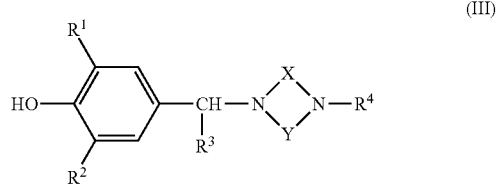

(III)

wherein
$R^1$, $R^2$, $R^3$ and $R^4$, as well as X are the same as described above; and
Y represents a divalent hydrocarbon group.

The aforementioned monovalent hydrocarbon group may be a monovalent saturated hydrocarbon group having 1 to 20 carbon atoms, preferably having 2 to 10 carbon atoms, and more preferably having 3 or 4 carbon atoms; or a monovalent unsaturated hydrocarbon group having 2 to 20 carbon atoms, preferably having 6 to 10 carbon atoms, and more preferably having 6 carbon atoms.

As examples of monovalent saturated hydrocarbon groups having 1 to 20 carbon atoms, mention may be made of linear or branched alkyl groups such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, and the like; as well as, cycloalkyl groups such as a cyclopropyl group, a cyclobutyl group, a cyclopentyl group, a cyclohexyl group, a cycloheptyl group, a cyclooctyl group, and the like.

The monovalent unsaturated hydrocarbon groups having 2 to 20 carbon atoms can be divided into monovalent unsaturated aliphatic hydrocarbon groups having 2 to 20 carbon atoms and monovalent aromatic hydrocarbon groups having 6 to 20 carbon atoms. As examples of monovalent unsaturated aliphatic hydrocarbon groups having 2 to 20 carbon atoms, mention may be made of linear or branched alkenyl groups such as a vinyl group, a 1-propenyl group, an allyl group, an isopropenyl group, a 1-butenyl group, a 2-butenyl group, a pentenyl group, a hexenyl group, and the like; as well as, cycloalkenyl groups such as a cyclopentenyl group, a cyclohexenyl group, and the like. As examples of monovalent aromatic hydrocarbon groups having 6 to 20 carbon atoms, mention may be made of a phenyl group, a benzyl group, a tolyl group, a xylyl group, a mesityl group, and the like.

As the aforementioned monovalent hydrocarbon group, one having steric hindrance is preferred. As the monovalent hydrocarbon groups having steric hindrance, for example, monovalent saturated hydrocarbon groups having steric hindrance such as an isopropyl group, an isobutyl group, a sec-butyl group, a tert-butyl group, and the like, as well as, monovalent aromatic hydrocarbon groups having steric hindrance such as a mesityl group and the like are preferred. In particular, a tert-butyl group and a mesityl group are preferred.

The alkyl group having 1 to 4 carbon atoms as the aforementioned $R^3$ and $R^9$ is a methyl group, an ethyl group, an n-propyl group, an isopropyl group, an n-butyl group, an isobutyl group, a sec-butyl group, or a tert-butyl group. As the aforementioned $R^3$ and $R^9$, a hydrogen atom is preferred.

The aforementioned divalent hydrocarbon group may be a divalent saturated hydrocarbon group having 1 to 6 carbon atom, preferably having 1 to 4 carbon atoms, and more preferably having 1 or 2 carbon atoms; or a divalent unsaturated hydrocarbon group having 2 to 10 carbon atoms, preferably having 6 to 10 carbon atoms, and more preferably having 6 or 7 carbon atoms.

As examples of divalent saturated hydrocarbon groups having 1 to 6 carbon atoms, mention may be made of linear or branched alkylene groups such as a methylene group, an ethylene group, a propylene group, an isopropylene (—$CH_2$—$CH(CH_3)$—) group, an n-butylene group, an isobutylene (—$CH_2$—$CH(CH_3)$—$CH_2$—) group, a sec-butylene (—$CH(CH_3)$—$CH_2$—$CH_2$—) group, a tert-butylene (—$CH_2$—$C(CH_3)_2$—) group, a pentylene group, a hexylene group, and the like.

The divalent unsaturated hydrocarbon groups having 2 to 10 carbon atoms can be divided into divalent unsaturated aliphatic hydrocarbon groups having 2 to 10 carbon atoms and divalent aromatic hydrocarbon groups having 6 to 10 carbon atoms. As examples of divalent unsaturated aliphatic hydrocarbon groups having 2 to 10 carbon atoms, mention may be made of alkenylene groups such as a vinylene group and the like. As examples of divalent aromatic hydrocarbon groups having 6 to 10 carbon atoms, mention may be made of arylene groups such as a phenylene group, a benzylene group and the like.

As the aforementioned divalent hydrocarbon group, a divalent saturated hydrocarbon group having 1 to 6 carbon atoms is preferred. A methylene group or an ethylene group is more preferred, and in particular, an ethylene group is preferred.

As examples of the aforementioned monovalent organic groups, mention may be made of, in addition to the aforementioned monovalent hydrocarbon groups, for example, monovalent functional groups such as a hydrogen atom, a halogen atom, a hydroxyl group, a $C_1$-$C_6$ alkoxy group, an amino group, a $C_1$-$C_6$ alkylamino group, a nitro group, a carbonyl group, an acyl group, a carboxyl group, a cyano group and the like; as well as monovalent substituted hydrocarbon groups such as halogenated $C_1$-$C_6$ alkyl groups such as a chloromethyl group, a 3-chloropropyl group, a 3,3,3-trifluoropropyl group, and the like; hydroxy($C_1$-$C_6$ alkyl) groups such as a hydroxymethyl group, a hydroxyethyl group, and the like; ($C_1$-$C_6$ alkoxy)($C_1$-$C_6$ alkyl) groups such as a methoxymethyl group, an ethoxymethyl group, a methoxyethyl group, an ethoxyethyl group, and the like; amino ($C_1$-$C_6$ alkyl) groups such as an aminomethyl group, an aminoethyl group and the like; and the like. The preferable monovalent organic group is a monovalent hydrocarbon group. An alkyl group is more preferred and an ethyl group and a methyl group are, in particular, preferred.

The aforementioned n and m can be independently any integer ranging from 1 to 4, is preferably 1 or 2, and is more preferably 1.

The compound of the present invention can be produced by means of the following method.

A phenol derivative represented by the following general formula (IV):

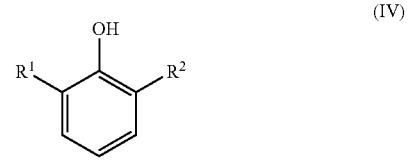
(IV)

wherein $R^1$ and $R^2$ are the same as described above, and a primary amine represented by the following general formula (V):

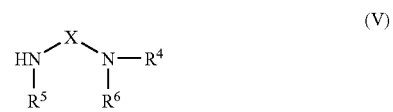
(V)

wherein X and $R^4$ to $R^6$ are the same as described above, or a secondary amine represented by the following formula (VI):

(VI)

wherein $R^4$ as well as X and Y are the same as described above, are mixed with an aldehyde in an alcohol-based solvent, and they are reacted under an inert gas atmosphere at a reflux temperature preferably ranging from 50° C. to 150° C. The reaction is continued until disappearance of the raw materials is confirmed, followed by cooling. Subsequently, purification such as recrystallization or the like using an appropriate solvent is preferably carried out.

As the aforementioned aldehyde, formaldehyde, acetoaldehyde, propionaldehyde or butylaldehyde can be used. Formaldehyde is preferred. In the case of using formaldehyde, formaldehyde is, in particular, preferably used in the form of an aqueous solution.

In the compound of the aforementioned general formula (I) of the present invention, when $R^4$ is a group of the aforementioned general formula (II), a primary amine in which $R^4$ of general formula (V) is a hydrogen atom is used in an amount of 0.5 equivalents.

In the compound of the aforementioned general formula (I), when $R^5$ and/or $R^6$ are/is a group of the aforementioned general formula (II), a primary amine in which $R^5$ and/or $R^6$ of general formula (V) are/is a hydrogen atom is used in an amount of 0.5 equivalents.

In the compound of the aforementioned general formula (III) of the present invention, when $R^4$ is a group of the aforementioned general formula (II), a secondary amine in which $R^4$ of general formula (VI) is a hydrogen atom is used in an amount of 0.5 equivalents.

As the aforementioned alcohol-based solvent, for example, an alcohol having 1 to 4 carbon atoms such as methanol, ethanol, propyl alcohol, isopropyl alcohol, or the like, as well as, a mixture of the aforementioned alcohol and water can be used. Isopropyl alcohol or a mixture of isopropyl alcohol and water is preferred.

The solvent for use in the aforementioned recrystallization is not particularly limited, and a ketone-based solvent such as acetone or the like, as well as, a mixture of the aforementioned ketone-based solvent and water can be used. Acetone or a mixture of acetone and water is preferred.

The compound of the present invention can be utilized as a component of, for example, a polymerization inhibitor. In particular, the compound of the present invention is preferably used as a polymerization inhibitor of a silicon-containing compound containing an acryloxy group or methacryloxy group. Among these, the compound of the present invention can be preferably used as a polymerization inhibitor for an acryloxysilane, methacryloxysilane, or the like.

The aforementioned acryloxysilane or methacryloxysilane respectively possesses an acryloxy moiety ($CH_2$=CH—COO—) or a methacryloxy moiety ($CH_2$=C($CH_3$)—COO—). The aforementioned acryloxy moiety or methacryloxy moiety directly binds to a silicon atom of an organosilane having an alkoxy group or a halogen atom or binds thereto via an alkylene group or an oxyalkylene group.

The aforementioned acryloxysilane or methacryloxysilane can be represented by, for example, the following general formula (VII):

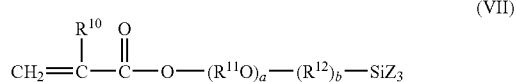

(VII)

wherein
$R^{10}$ represents a hydrogen atom or a methyl group;
$R^{11}$ represents an alkylene group having 1 to 6 carbon atoms;
$R^{12}$ represents an alkylene group having 1 to 6 carbon atoms;
  each of the Zs independently represents an alkyl group, an alkoxy group, an alkoxyalkoxy group, or an alkoxyalkyl group, having 1 to 6 carbon atoms, an aryl group having 6 to 18 carbon atoms, an aralkyl group having 7 to 20 carbon atoms, an acetoxy group, or a halogen atom;

a represents 0 or an integer ranging from 1 to 10; and
b represents 0 or an integer ranging from 1 to 10,
with the proviso that a+b is 1 or more.

As examples of the aforementioned alkyl groups having 1 to 6 carbon atoms, mention may be made of linear or branched alkyl groups such as a methyl group, an ethyl group, an n-propyl group, an isopropyl group, an n-butyl group, an isobutyl group, a sec-butyl group, a tert-butyl group, a pentyl group, a hexyl group and the like; cycloalkyl groups such as a cyclopropyl group, a cyclobutyl group, a cyclopentyl group, a cyclohexyl group, and the like.

As examples of the aforementioned alkoxy groups having 1 to 6 carbon atoms, mention may be made of a methoxy group, an ethoxy group, a propoxy group, an isopropoxy group, an n-butoxy group, a sec-butoxy group, a tert-butoxy group and the like. A methoxy group or an ethoxy group is preferred, and a methoxy group is more preferred.

As examples of the aforementioned alkoxyalkoxy groups having 1 to 6 carbon atoms, mention may be made of a methoxymethoxy group, an ethoxymethoxy group, a methoxyethoxy group, an ethoxyethoxy group and the like.

As the aforementioned alkoxyalkyl groups having 1 to 6 carbon atoms, mention may be made of a methoxymethyl group, an ethoxymethyl group, a methoxyethyl group, an ethoxyethyl group and the like.

As examples of the aforementioned aryl groups having 6 to 18 carbon atoms, mention may be made of a phenyl group, a tolyl group, a xylyl group, a naphtyl group and the like.

As examples of aralkyl groups having 7 to 20 carbon atoms, mention may be made of a benzyl group, a 2-phenylethyl group, a 3-phenylpropyl group and the like.

The aforementioned halogen atom is a fluorine atom, a chlorine atom, a bromine atom or an iodine atom, and a chlorine atom is preferred.

As examples of the aforementioned alkylene groups having 1 to 6 carbon atoms, mention may be made of linear or branched alkylene groups such as a methylene group, an ethylene group, a propylene group, an isopropylene (—$CH_2$—CH($CH_3$)—) group, an n-butylene group, an isobutylene (—$CH_2$—CH($CH_3$)—$CH_2$—) group, a sec-butylene (—CH($CH_3$)—$CH_2$—$CH_2$—) group, a tert-butylene (—$CH_2$—C($CH_3$)$_2$—) group, a pentylene group, a hexylene group, and the like.

The aforementioned a and b can be independently 0 or an integer ranging from 1 to 10, and 0 or an integer ranging from 1 to 4 is preferred. The case in which a is 0 and b is 3 or 4 is more preferred.

As examples of the aforementioned acryloxysilane or methacryloxysilane, without limitation, mention may be made of 3-acryloxypropyltrimethoxysilane, 3-acryloxypropyl-triethoxysilane, 3-methacryloxypropyltrimethoxysilane, 3-methacryloxyisobutyl-trimethoxysilane, 3-methacryloxypropyl-triethoxysilane, 3-acryloxypropyltrichlorosilane, 3-methacryloxypropyltrichlorosilane, 3-methacryloxyisobutyl-trichlorosilane, 3-methacryloxypropyl[tris(β-methoxyethoxy)]silane, 3-methacryloxypropyldimethylchlorosilane, 3-methacryloxypropylmethyldichlorosilane, 3-acryloxypropyl-dimethylchlorosilane, 3-acryloxypropylmethyldichlorosilane, 3-acryloxypropylmethyldimethoxysilane, 3-acryloxypropyl-methyldiethoxysilane, 3-methacryloxypropylmethyl-dimethoxysilane, 3-methacryloxypropylmethyldiethoxysilane, 3-acryloxypropyl-phenyldimethoxysilane, 3-acryloxypropyl-phenyldiethoxysilane, 3-methacryloxypropylphenyl-dimethoxysilane, 3-methacryloxy-propylphenyldiethoxysilane, 3-acryloxypropyltriacetoxysilane, 3-methacryloxypropyl-triacetoxysilane, and the like.

The preparation method for the aforementioned acryloxysilane or methacryloxysilane is not particularly limited, and any preparation methods known to a person skilled in the art can be used.

For example, the aforementioned acryloxysilane or methacryloxysilane can be obtained by a method in which an acrylate or methacrylate of an aliphatic unsaturated bond-containing alcohol and an organosilane containing a hydrogen atom binding to a silicon atom are subjected to an addition reaction, and subsequently, from the obtained mixture, the objective acryloxysilane or methacryloxysilane is isolated by purification under distillation; a method in which an alkali metal salt of acrylic acid or an alkali metal salt of methacrylic acid is reacted with a halogen-substituted organic group-containing organosilane in the presence of a basic catalyst, and subsequently, from the obtained mixture, the objective acryloxysilane or methacryloxysilane is isolated by purification under distillation; and the like.

The aforementioned method for purification under distillation is not particularly limited. In order to prevent polymerization of the acryl group or methacryl group due to heat, a method for purification under distillation with good efficiency is preferred. As the aforementioned method for purification under distillation, molecular distillation may be mentioned. The conditions of molecular distillation are suitably determined in accordance with a distillation objective or quality of a product to be produced. The pressure conditions preferably range from 0.001 to 10.0 mmHg. The distillation temperature preferably ranges from 40 to 150° C., and in particular, preferably ranges from 80 to 120° C. The liquid to be distilled is converted into a filmy state with a thickness ranging from 0.05 to 5.0 mm, and evaporation is carried out for a heating period ranging from 0.1 to 5.0 seconds. When the evaporated components are trapped, the temperature of the first cooler of a distillation apparatus appropriately ranges from −5° C. to 30° C., and the temperature of the second cooler is preferably −40° C. or less.

Therefore, the compound of the present invention is preferably used together with a silicon-containing compound containing an acryloxy group or methacryloxy group such as acryloxysilane, methacryloxysilane, or the like. For example, the compound of the present invention can be added to a silane coupling agent containing an acryloxysilane or methacryloxysilane. Thereby, the polymerization of acryloxysilane or methacryloxysilane in the aforementioned silane coupling agent can be controlled for a long time. Thereby, increasing viscosity during storage of a silane coupling agent can be prevented, and usability can be maintained.

In addition, the compound of the present invention may be blended at the time of preparation or distillation production of a silicon-containing compound containing an acryloxy group or methacryloxy group. As examples of the silicon-containing compound containing an acryloxy group or methacryloxy group, mention may be made of, for example, an acryloxysilane or a methacryloxysilane. The compound of the present invention can effectively prevent non-preferable polymerization reactions at the time of production or purification by distillation of a silicon-containing compound containing an acryloxy group or methacryloxy group, as a polymerization inhibitor.

The compound of the present invention is, in particular, effective as a polymerization inhibitor in a method in which an acrylate or methacrylate of an aliphatic unsaturated bond-containing alcohol and a Silicon-containing compound containing a hydrogen atom binding to a silicon atom are subjected to an addition reaction, and subsequently, from the obtained mixture, a desirable silicon-containing compound containing an acryloxy group or methacryloxy group is isolated by purification under distillation.

As examples of the aforementioned acrylate or methacrylate of the aliphatic unsaturated bond-containing alcohol, mention may be made of allyl acrylate, allyl methacrylate, isobutenyl acrylate, isobutenyl methacrylate, hexenyl acrylate, hexenyl methacrylate, allyloxyethyl acrylate, allyloxyethyl methacrylate, styryl acrylate, styryl methacrylate and the like.

As the aforementioned silicon-containing compound containing a hydrogen atom binding to a silicon atom, an organosilane containing a hydrogen atom binding to a silicon atom may be mentioned. As examples thereof, mention may be made of trialkoxysilanes such as trimethoxysilane, triethoxysilane, tri-tert-butoxysilane and the like; trichlorosilane; trialkoxyalkoxysilanes such as [tris(β-methoxyethoxy)]silane and the like; dimethylchlorosilane; methyldichlorosilane; methyldialkoxysilanes such as methyldimethoxysilane, methyldiethoxysilane and the like; phenyldialkoxysilanes such as phenyldimethoxysilane, phenyldiethoxysilane and the like; triacetoxysilane; methyldiacetoxysilane; and the like.

The compound of the present invention can be used as it is or in the state of dissolving or dispersing in a solvent such as water, alcohol, acetone, benzene, toluene, xylene or the like. The compound of the present invention exhibits increased water-solubility under acidic conditions, as compared with a conventional hindered phenol-based polymerization inhibitor such as 2,6-di-tert-butyl-4-dimethylaminomethylphenol or the like. For this reason, the compound can be used by dissolving a mixture of, for example, acetic acid and water (acetic acid:water=0.2:100). Acetic acid acts as a catalyst of a hydrolysis reaction of the alkoxy group of the acryloxysilane or methacryloxysilane to accelerate the production of a water-soluble silanol compound. In addition, acetic acid has an action for delaying the production of a water-insoluble polymer due to a dehydration condensation reaction of the aforementioned silanol compound, and prolonging the life of the silane coupling agent.

The compound of the present invention can also be utilized as a component of an antioxidant or an antiaging agent, as well as, a thermal stabilizer or a processing stabilizer, in addition to a polymerization inhibitor.

The polymerization inhibitor, antioxidant, and thermal stabilizer may be formed from only the compound of the present invention, or alternatively may contain other components. The blending amount of the compound of the present invention in the polymerization inhibitor, antioxidant, or thermal stabilizer is not particularly limited, and can range, for example, from 1 to 100% by weight, from 10 to 90% by weight, from 20 to 80% by weight, or from 30 to 70% by weight. As the compound of the present invention, a single compound represented by the aforementioned general formula (I) or (III) may be used, or alternatively, a mixture of two or more types of the compounds may be used.

When the polymerization inhibitor, antioxidant, and thermal stabilizer contain components other than the compound of the present invention, as the other components, other polymerization inhibitor components, other antioxidant components, and other thermal stabilizer components may be respectively contained. The blending amount of the other polymerization inhibitor components, the other antioxidant components and the other thermal stabilizer components is not particularly limited, and may range, for example, from 0.01 to 20% by weight, from 0.1 to 10% by weight, or from 1 to 5% by weight.

As examples of other polymerization inhibitor components, mention may be made of, for example, in addition to quinone-based compounds such as hydroquinone, benzoquinone and the like, hindered phenols such as 2,6-di-t-butylphenol, 2,6-di-t-butyl-p-cresol, 2,6-di-t-butyl-4-dimethylaminomethylphenol and the like.

As examples of other antioxidants, mention may be made of, in addition to the aforementioned hindered phenols, for example, aromatic amine compounds such as phenyl-α-naphthylamine, 4,4'-dioctylphenylamine, N,N'-di-β-naphthyl-p-phenylenediamine, N,N'-diphenyl-p-phenylenediamine, N-phenyl-N'-cyclohexyl-p-phenylenediamine, N,N'-di-o-tolylethylenediamine and the like.

As examples of other thermal stabilizer components, mention may be made of, in addition to the aforementioned hindered phenol, for example, organic acid salts such as stearate, maleate, salicylate, and the like; inorganic acid salts such as sulfate, carbonate, silicate, and the like; organotin compounds; epoxy compounds and the like.

The silane coupling agent containing the compound of the present invention, as well as, the polymerization inhibitor, antioxidant, and thermal stabilizer formed from the compound of the present invention can be preferably blended in a polymerizable compound or a polymer.

The aforementioned polymerizable composition is not particularly limited, and any compositions can be used, as long as they have a property of producing a polymer by polymerization under appropriate conditions. As examples of the aforementioned polymerizable compositions, typically mention may be made of a composition containing an organic monomer as a main component.

The aforementioned polymerizable composition can contain an inorganic filler such as silica, alumina, glass, mica, talc, clay or the like, or an organic filler such as silicone fine powders or the like. In addition, the aforementioned polymerizable composition can be in the form of an adhesive, paint, sealant or the like.

The aforementioned polymerizable composition may be a thermosetting resin. As examples of the thermosetting resins, mention may be made of, for example, an unsaturated polyester resin, a diallyl phthalate resin and the like.

The aforementioned polymer may be a thermoplastic resin or an elastomer. As examples of thermoplastic resins, mention may be made of, for example, acryl resin, methacryl resin, polyolefin, polystyrene, polyvinyl chloride and the like. As examples of elastomers, mention may be made of, for example, polybutadiene, EPM, EPDM and the like. The aforementioned polymer may be an organosilicon polymer such as organopolysiloxane or the like.

The aforementioned polymerizable composition or polymer can be formulated into various molded products by a known molding means. The molding means is not particularly limited. Various molding means such as injection molding, compression molding, injection compression molding, extrusion molding, blow molding, cast molding and the like, can be used.

EXAMPLES

Synthesis Example 1

In a three-necked flask with a volume of 300 ml, equipped with a nitrogen gas inlet tube, a reflex condenser, a thermometer, and a stirrer, 20.6 g (0.10 mol) of 2,6-di-t-butylphenol, 8.5 g (0.105 mol) of a 37% aqueous solution of formaldehyde, 10.2 g (0.10 mol) of N,N,N'-trimethylethylene-diamine, and 80 g of isopropyl alcohol were placed. The mixture was reacted for 2.5 hours under refluxing. The solvents and unreacted materials were removed under reduced pressure. The residue was purified by recrystallization in an acetone solvent. Thereby, a compound represented by the following formula:

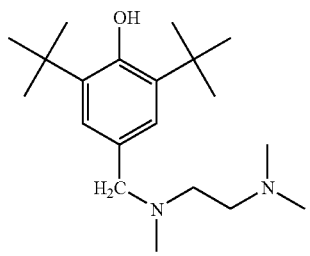 [SMILES: CN(C)CCN(C)Cc1cc(C(C)(C)C)c(O)c(C(C)(C)C)c1]

was obtained in an amount of 17 g (yield: 53%).

Synthesis Example 2

In a three-necked flask with a volume of 300 ml, equipped with a nitrogen gas inlet tube, a reflex condenser, a thermometer, and a stirrer, 20.6 g (0.10 mol) of 2,6-di-t-butylphenol, 8.5 g (0.105 mol) of a 37% aqueous solution of formaldehyde, 10.0 g (0.10 mol) of N-methylpiperazine, and 80 g of isopropyl alcohol were placed. The mixture was reacted for 14 hours under refluxing. The solvents and unreacted materials were removed under reduced pressure. The residue was purified by recrystallization in an acetone-water (7:3) mixture solvent. Thereby, a compound represented by the following formula:

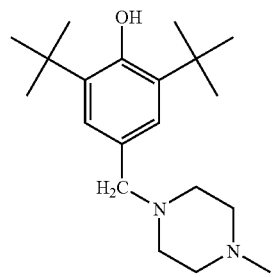 [SMILES: CN1CCN(Cc2cc(C(C)(C)C)c(O)c(C(C)(C)C)c2)CC1]

was obtained in an amount of 24 g (yield: 75%).

Example 1

In a vial made of glass with a volume of 20 ml, 5 g of 3-methacryloxypropyltrichlorosilane containing no polymerization inhibitor, and 0.005 g (1,000 ppm) of the compound obtained in Synthesis Example 1 as a polymerization inhibitor were added. Visual observation of the presence or absence of gelation at 150° C. was carried out, and a period for occurrence of gelation was measured. The results are shown in Table 1.

Comparative Example 1

In a vial made of glass with a volume of 20 ml, 5 g of 3-methacryloxypropyltrichlorosilane containing no polymerization inhibitor, and 0.005 g (1,000 ppm) of 2,6-di-t-butyl-p-cresol as a polymerization inhibitor were added. Visual observation of the presence or absence of gelation in the vial at 150° C. was carried out, and the period for occurrence of gelation was measured. The results are shown in Table 1.

TABLE 1

| | Polymerization inhibitor | Period for occurrence of gelation |
|---|---|---|
| Example 1 | Compound obtained in Synthesis Example 1 | Never gelled in 10 hours or more |
| Comparative Example 1 | 2,6-di-t-butyl-p-cresol | Gelled in 0.5 hours |

From the results shown in Table 1, it can be seen that the compound obtained in Synthesis Example 1 exhibits increased effects of inhibiting polymerization, as compared with 2,6-di-t-butyl-p-cresol, which is known as a conventional polymerization inhibitor.

Example 2

In a vial made of glass with a volume of 20 ml, containing 5 g of 3-methacryloxypropyltrimethoxysilane containing no polymerization inhibitor, 0.005 g (1,000 ppm) of a compound obtained in Synthesis Example 2 (1-(3,5-di-t-butyl-4-hydroxybenzyl)-4-methylpiperazine) as a polymerization inhibitor was added. An acceleration test therefor was carried out for 28 hours at 180° C., and further carried out for 168 hours at 25° C. Visual observation of the degree of gelation was carried out. The results are shown in Table 2.

Comparative Example 2

In a vial made of glass with a volume of 20 ml, 5 g of 3-methacryloxypropyltrimethoxysilane containing no polymerization inhibitor, and 0.005 g (1,000 ppm) of 2,6-di-t-butyl-p-cresol as a polymerization inhibitor were added. An acceleration test therefor was carried out for 28 hours at 180° C., and further carried out for 168 hours at 25° C. Visual observation of the degree of gelation was carried out. The results are shown in Table 2.

Comparative Example 3

In a vial made of glass with a volume of 20 ml, 0.5 g of 3-methacryloxypropyltrimethoxysilane containing no polymerization inhibitor, and 0.005 g (1,000 ppm) of 2,6-di-t-butyl-4-dimethylaminomethylphenol as a polymerization inhibitor were added. An acceleration test therefor was carried out for 28 hours at 180° C., and further carried out for 168 hours at 25° C. Visual observation of the degree of gelation in the vial was carried out. The results are shown in Table 2.

TABLE 2

| | Polymerization inhibitor | Period for occurrence of gelation |
|---|---|---|
| Example 2 | Compound obtained in Synthesis Example 2 | No gelation Small increase in viscosity |
| Comparative Example 2 | 2,6-di-t-butyl-p-cresol | Slight gelation Large increase in viscosity |
| Comparative Example 3 | 2,6-di-t-butyl-4-dimethylaminomethylphenol | Slight gelation Large increase in viscosity |

From the results shown in Table 2, it can be seen that the compound obtained in Synthesis Example 2 exhibits superior effects of inhibiting polymerization, as compared with 2,6-di-t-butyl-p-cresol and 2,6-di-t-butyl-4-dimethylaminomethylphenol, which are known as conventional polymerization inhibitors.

Example 3

In a three-necked flask with a volume of 100 ml, equipped with a nitrogen gas inlet tube, a reflex condenser, a thermometer, and a stirrer, 25.8 g (0.204 mol) of allyl methacrylate, 0.2 g (platinum content=0.4 mmol) of a solution of a platinum-divinyltetramethylsiloxane complex, and 0.1 g of 1-(3,5-di-t-butyl-4-hydroxybenzyl)-4-methylpiperazine obtained in Synthesis Example 2 were placed. The mixture was heated to 80° C., and 21.2 g (0.2 mol) of methyldimethoxysilane was added dropwise thereto. Subsequently, the mixture was stirred for 0.5 hours at 80° C. In addition, 0.04 g of dibutylhydroxytoluene was added thereto. The reaction mixture was distilled under a reduced pressure of 1 mm Hg, and thereby, a fraction at 68 to 71° C. was obtained. The obtained fraction was methacryloxypropylmethyldimethoxysilane, and the amount thereof was 35.2 g (yield: 74.8%).

Comparative Example 4

The same operations as described in Example 3 were carried out with the exception of using phenothiazine instead of 1-(3,5-di-t-butyl-4-hydroxybenzyl)-4-methylpiperazine obtained in Synthesis Example 2. As a result, when 3 g of methyldimethoxysilane was added dropwise thereto, the solution in the flask gelled. Therefore, the desirable compound (methacryloxypropylmethyldimethoxysilane) could not be obtained.

From the results described in Example 3 and Comparative Example 4, it can be seen that the compound obtained in Synthesis Example 2 exhibits superior effects of inhibiting polymerization, as compared with phenothiazine, which is known as a conventional polymerization inhibitor.

The invention claimed is:

1. A composition comprising:
   acryloxysilane or methacryloxysilane; and
   a compound represented by the following general formula (I):

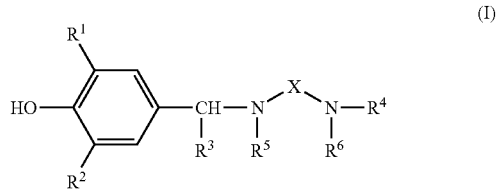

wherein
R$^1$ and R$^2$ independently represent a monovalent hydrocarbon group;
R$^3$ represents a hydrogen atom or an alkyl group having 1 to 4 carbon atoms;
X represents a divalent hydrocarbon group; and
R$^4$, R$^5$ and R$^6$ independently represent a monovalent saturated hydrocarbon group,
with the proviso that R$^5$ and R$^6$ may combine together to form a divalent saturated hydrocarbon group.

2. The composition according to claim 1, wherein the compound represented by general formula (I) is represented by the following general formula (III):

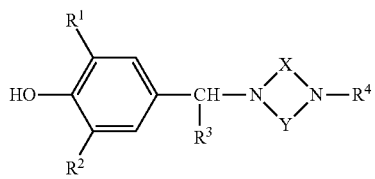

(III)

wherein
$R^1$, $R^2$, $R^3$ and $R^4$, as well as X are the same as described above; and
Y represents a divalent saturated hydrocarbon group.

3. The composition according to claim 1 which is a silane coupling agent.

4. The composition according to claim 1, which is polymerizable and further comprises an organic monomer.

5. A polymer comprising the composition as recited in claim 1.

6. A molded product obtained from the polymerizable composition as recited in claim 4.

7. A method for producing a silicon-containing compound containing an acryloxy group or a methacryloxy group comprising producing the same in the presence of the compound represented by the following general formula (I):

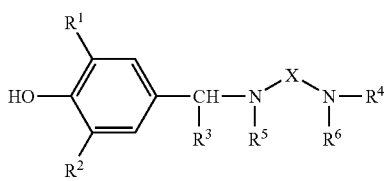

(I)

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent saturated hydrocarbon group,
with the proviso that $R^5$ and $R^6$ may combine together to form a divalent saturated hydrocarbon group.

8. The method according to claim 7, wherein said silicon-containing compound containing an acryloxy group or a methacryloxy group is an acryloxysilane or a methacryloxysilane.

9. A method for producing an acryloxysilane or a methacryloxysilane, comprising addition-reacting an acrylate or methacrylate of an alcohol containing an aliphatic unsaturated bond with an organosilane containing a hydrogen atom binding to a silicon atom, in the presence of the compound represented by the following general formula (I):

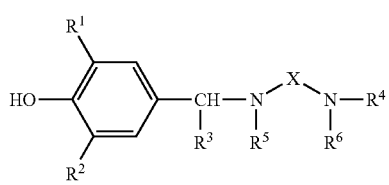

(I)

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent saturated hydrocarbon group,
with the proviso that $R^5$ and $R^6$ may combine together to form a divalent saturated hydrocarbon group.

10. The method for producing an acryloxysilane or a methacryloxysilane according to claim 9, wherein said organosilane containing a hydrogen atom binding to a silicon atom is a methyldialkoxysilane.

11. A method for producing an acryloxysilane or a methacryloxysilane, comprising the step of purifying an acryloxysilane or a methacryloxysilane by distillation in the presence of the compound represented by the following general formula (I):

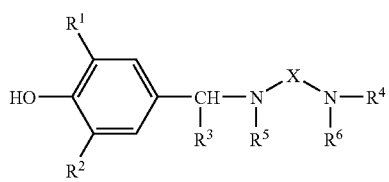

(I)

wherein
$R^1$ and $R^2$ independently represent a monovalent hydrocarbon group;
$R^3$ represents a hydrogen atom or an alkyl group having 1 to 4 carbon atoms;
X represents a divalent hydrocarbon group; and
$R^4$, $R^5$ and $R^6$ independently represent a monovalent saturated hydrocarbon group,
with the proviso that $R^5$ and $R^6$ may combine together to form a divalent saturated hydrocarbon group.

12. A molded product obtained from the polymer as recited in claim 5.

* * * * *